United States Patent

Eppler et al.

[11] Patent Number: 5,866,324
[45] Date of Patent: Feb. 2, 1999

[54] METHOD OF DETECTING EXPRESSION OF PROTEINS CLOSELY RELATED TO OPIOID RECEPTORS

[75] Inventors: C. Mark Eppler, Langhorne; Bradley A. Ozenberger, Yardley, both of Pa.; Jeffrey D. Hulmes, Ringwood, N.J.

[73] Assignee: American Cyanamid Company, Wayne, N.J.

[21] Appl. No.: 454,549

[22] Filed: May 30, 1995

Related U.S. Application Data

[63] Continuation-in-part of Ser. No. 185,360, filed as PCT/US95/00939 Jan. 20, 1995, abandoned.

[51] Int. Cl.$^6$ .............................. C12Q 1/68; C12P 19/34; C07H 19/00; C07K 1/00
[52] U.S. Cl. ........................... 435/6; 435/91.1; 435/91.2; 435/91.21; 536/221; 536/24.3; 530/350
[58] Field of Search .............................. 435/6, 91.1, 91.2, 435/91.21; 536/22.1, 24.3; 530/350

[56] References Cited

U.S. PATENT DOCUMENTS

| | | | |
|---|---|---|---|
| 5,242,822 | 9/1993 | Marullo et al. | 435/252.3 |
| 5,389,543 | 2/1995 | Bunzow et al. | 435/252.3 |
| 5,658,783 | 8/1997 | Grandy et al. | 435/325 |

FOREIGN PATENT DOCUMENTS

WO95/19986  7/1995  WIPO.

OTHER PUBLICATIONS

Wang, J.B., et al. (1993), "μ Opiate Receptor: cDNA cloning and Expression", *Proc. Natl. Acad. Sci., USA,* vol. 90, pp. 10230–10234.

Y. Chen, et al. (1993), "Molecular Cloning and Functional Expression of a μ–Opioid Receptor from Rat Brain", *Mol. Pharmacol.* 44:8–12.

B. L. Keiffer (1992), "The S–opioid receptor: Isolation of a cDNA by expression cloning and Pharmacological Characterization", 89:12048–12052.

C. J. Evans et al. (1992), "Cloning of a Delta Opioid Receptor by Functional Expression", *Science* 258:1952–1955.

Bunzow, James R., et al. (1994), "Molecular cloning and Tissue distribution of a putative member of the rat opioid receptor gene family that is not a μ, δ or κ opioid receptor type", *FEBS Letters,* 347:284–288.

Fukuda K., et al. (1994), "cDNA cloning and regional distribution of a novel member of the opioid receptor family,", *Febs Letters,* 343:42–46.

Chen et al., "Molecular Cloning, Tissue Distribution and Chromosomal Localization of a Novel member of the Opioid Receptor Gene Family", *FEBS Letters,* 347:279–283; 280–281.

Wick et al. (1993), "Isolation of a Novel cDNA Encoding a Putative Member Receptor with High Homology to the Cloned μ, δ and κ Opioid Receptors" *Molecular Brain Research,* 27:37–44; 39–43.

Coscia et al. (1991), "A Monoclonal Anti–idiotypic Antibody to μ, and δ Opioid Receptors", *Molecular Brain Research* 9:299–306; 300–303.

Goldstein et al., *Opiods: Past, Present and Future,* 10:127–143, 1984.

Lord et al., *Nature,* 267:495–499, 1977.

(List continued on next page.)

*Primary Examiner*—Ardin H. Marschel
*Assistant Examiner*—Jezia Riley
*Attorney, Agent, or Firm*—Darby & Darby

[57] ABSTRACT

Isolated DNAs encoding opiorph receptor polypeptides are provided. Recombinant cloning vectors which include these DNA sequences and cells which include these vectors are also provided. Methods for detecting the expression, in a tissue, of mRNA encoding a polypeptide encoded by this DNA are encompassed as well as methods for producing these polypeptides. These isolated polypeptides and antibodies to these polypeptides are also contemplated.

2 Claims, 13 Drawing Sheets

```
MESLFPAPYW EVLYGSHFQG NLSLLNETVP HHLLLNASHS AFLPLGLKVT
IVGLYLAVCI GGILGNCLVM YVILRHTKMK

TATNIYIFNL ALADTLVLLT LPFQGTDILL GFWPFGNALC KTVIAIDYYN
MFTSTFTLTA MSVDRYVAIC HPIRALDVRT

SSKAQAVNVA IWALASVVGV PVAIMGSAQV EDEEIECLVE IPAPQDYWGP
VFAICIFLFS FIIPVLIISV CYSLMIRRLR

GVRLLSGSRE KDRNLRRITR LVLVVVAVFV GCWTPVQVFV LVQGLGVQPG
SETAVAILRF CTALGYVNSC LNPILYAFLD

ENFKACFRKF CCASSLHREM QVSDRVRSIA KDVGLGCKTS ETVPRPA
```

OTHER PUBLICATIONS

Schulz et al., *J. Pharmacol. Exp. Ther.*, 216:604–606, 1981.
Loh et al., *Ann. Rev. Phamacol. Toxicol.*, 30:123–147, 1990.
Birnbaumer et al., *Biochem. Biophys. Acta.*, 1031:163–224, 1990.
Bidlack et al., *PNAS USA*, 78:636–639, (1981).
Gioannini et al., *Molecular Pharmacology*, 44:396–801, 1993.
Maneckjee et al., *PNAS USA*, 82:594–598, 1985.
Cho et al., *PNAS USA*, 83:4138–4149, 1986.
Ahmed et al., *Life Sciences* 44:861–871, 1989.
Laemmli et al., *Nature,* 227:680–685, 1970.
Whitehead et al., *Nature,* 305:158–159, 1983.
Merril et al., *Science,* 211:1437–1438, 1981.
Wessel et al., *Anal. Bioch.,* 138:141–143, 1984.
Blume, *PNAS USA,* 75:1713–1717, 1978.
Childers et al., *Life Sciences,* 23:759–762, 1978.
Yinchang et al., *Proc. CAMS and PUMC,* 4:1–7, 1989.
Schofield et al., *EMBO J.,* 8:489–495, 1989.
Bidlack et al., *J. Biol. Chem.,* 261:15844–15849, 1985.
Bidlack et al., *J. Biol. Chem.,* 260:15655–15661, 1985.
Roy et al., *BBRC,* 150:237–244, 1988.
Roy et al., *BBRC,* 154:688–693, 1988.
Xie et al., *PNAS USA,* 89:4124–4128, 1992.
Libert et al., *Science,* 244:569–572, 1989.
Chow et al., *Mol. Pharmacol.,* 24:203–212, 1983.
Sambrook et al. (1989), *Molecular Cloning,* 2nd Ed., p. 16.3.
Ueda et al. (1988), "Reconstitution of rat brain $\mu$ opioid receptors . . . ", *P.N.A.S.* 85:7013–7017.

FIG. IA

GCGGCCGCCT TTCTGCTAAG CATTGGGGTC TATTTTGGCC CAGCTTCTGA
AGAGGCTGTG TGTGCCGTTG GAGGAACTGT

ACTGAGTGGC TTTGCAGGGT GACAGCATGG AGTCCCTCTT TCCTGCTCCA
TACTGGGAGG TCTTGTATGG CAGCCACTTT

CAAGGGAACC TGTCCCTCCT AAATGAGACC GTACCCCACC ACCTGCTCCT
CAATGCTAGT CACAGCGCCT TCCTGCCCCT

TGGACTCAAG GTCACCATCG TGGGGCTCTA CTTGGCTGTG TGCATCGGGG
GGCTCCTGGG GAACTGCCTC GTCATGTATG

TCATCCTCAG GCACACCAAG ATGAAGACAG CTACCAACAT TTACATATTT
AATCTGGCAC TGGCTGATAC CCTGGTCTTG

CTAACACTGC CCTTCCAGGG CACAGACATC CTACTGGGCT TCTGGCCATT
TGGGAATGCA CTCTGCAAGA CTGTCATTGC

TATCGACTAC TACAACATGT TTACCAGCAC TTTTACTCTG ACCGCCATGA
GCGTAGACCG CTATGTGGCT ATCTGCCACC

FIG. 1B

CTATCCGTGC CCTTGATGTT CGGACATCCA GCAAAGCCCA GGCTGTTAAT
GTGGCCATAT GGGCCCTGGC TTCAGTGGTT

GGTGTTCCTG TTGCCATCAT GGGTTCAGCA CAAGTGGAAG ATGAAGAGAT
CGAGTGCCTG GTGGAGATCC CTGCCCCTCA

GGACTATTGG GGCCCTGTAT TCGCCATCTG CATCTTCCTT TTTTCCTTCA
TCATCCCTGT GCTGATCATC TCTGTCTGCT

FIG. 1C

ACAGCCTCAT GATTCGACGA CTTCGTGGTG TCCGTCTGCT TTCAGGCTCC
CGGGAGAAGG ACCGAACCT GCGGCGTATC

ACTCGACTGG TGCTGGTAGT GGTGGCTGTG TTTGTGGGCT GCTGGACGCC
TGTGCAGGTG TTTGTCCTGG TTCAAGGACT

GGGTGTTCAG CCAGGTAGTG AGACTGCAGT TGCCATCCTG CGCTTCTGCA
CAGCCCCTGGG CTATGTCAAC AGTTGTCTCA

ATCCCATTCT CTATGCTTTC CTGGATGAGA ACTTCAAGGC CTGCTTTAGA
AAGTTCTGCT GTGCTTCATC CCTGCACCGG

GAGATGCAGG TTTCTGATCG TGTGCGGAGC ATTGCCAAGG ATGTTGGCCT
TGGTTGCAAG ACTTCTGAGA CAGTACCACG

GCCAGCATGA CTAGGCGTGG ACCTGCCCAT GGTGCCTGTC AGCCCACAGA
GCCCATCTAC ACCCAACACG GAGCTCACAC

AGGTCACTGC TCTCTAGGTT GACCCTGAAC CTTGAGCATC TGGAGCCTTG
AATGGCTTTT CTTTTGGATC AGGATGCTCA

GTCCTAGAGG AAGACCTTTT AGCACCATGG GACAGGTCAA AGCATCAAGG
TGGTCTCCAT GGCCTCTGTC AGATTAAGTT

CCCTCCCTGG TATAGGACCA GAGAGGACCA AAGGAACTGA ATAGAAACAT
CCACAACACA GTGGACATGC CTGGTGAGCC

CATGTAGGTA TTCATGCTTC ACTTGACTCT TCTCTGGCTT CTCCCTGCTG
CCCTGGCTCT AGCTGGGCTC AACCTGAGGT

ATTGTAGTGG TCATGTAGTC ACTCTTGTGA CTACATGTTG TGTGCTGTTG
CTCTCGGCCT TTCAGTATTT CCACAGGACT

FIG. 1D

GCTGAACATA CCTGGTATTG CAGTGGGGAG CATTAATTTT CTTTTAAAGT
GAGACTGGCC CTTAAGCTTG GCGTTGCCTT

GGAGCGTCTT CTACTTCTGA CTTCACTGAT GCAGTCAGAT TACCCGAGGG
TGAGCATCAG TGGTTTCTTG GATGGCTGTT

TTCTGAAGAT TCTTCCCATC CAGTACATGG AGTCTATGAA GGGGAGTCAC
AATTCATCTG GTACTGCCAC TACCTGCTCT

FIG. IE

ATAATCCTGG GCTATCTTCT TGGCAAGATG ACAGTGGGGG AGACAAGACA
CAGAGCTTCC CTAAGGCTCT TTCCCTCCAA

AACCACTGTG AACTCTTATC CTACAGACTG TTCGGCAAGC ACTGCTTCTA
GGTGTGTGGG AGGTAATCAG GAGAAAGCTT

TGTGGCCTCT GTAGGCTGCT CACAACATGG AGGCACCACA TGCTGGTCTT
GCCTGCTTAG TACAGGCAGG ACAGAGCAGA

ATATGCTCTC TCTCGATTCT CTACAAACTC CCTCAGTTCT CCAGCAGAGT
CTCTTTTACT TGCTATCAGA GGTCAGGAGT

TGTACTGCTA GAAGCATACT TGTAGCTTGG GAAGAGTGGC AGTCAGGATG
TGTTCTACTC TATATCCACA GTGACCACCT

GCTTCATATA TAGGGTTAGG ACATATCTGA GTAAGGCCTG AGTGTGCTGC
CAAATTGGAG GTTGGTATGA GAGCTGATGC

CTAAAGTGGC TCATTTGCAA GGACTATTAT GGTTTGGAAT AGCAATGGGG
GGCATGGGAA GAAGAGTCTA TACCTTGGAG

FIG. IF

```
ATCTATTTGA TGGTTCACAG AAGAGGTTTT GTAAACGCCC TTTCTATGGG
TCAGATATCA AAATACCAGC AACGTTGGAT

AGATTCTGAC CTTTTACTGA GACCTCGGTC AGATGGTTTC ATGTCATGCA
GAGAACCTAG GCTGGTTCCT GTGTCAGAGA

GACCTGGGCT TCTGGGGAGG CCAGGGTTCT TCCTTTGACA CTTGTGCGGG
AGCCGTTAGC TCTAGA
```

FIG. 2

MESLFPAPYW EVLYGSHFQG NLSLLNETVP HHLLLNASHS AFLPLGLKVT
IVGLYLAVCI GGILGNCLVM YVILRHTKMK

TATNIYIFNL ALADTLVLLT LPFQGTDILL GFWPFGNALC KTVIAIDYYN
MFTSTFTLTA MSVDRYVAIC HPIRALDVRT

SSKAQAVNVA IWALASVVGV PVAIMGSAQV EDEEIECLVE IPAPQDYWGP
VFAICIFLFS FIIPVLIISV CYSLMIRRLR

GVRLLSGSRE KDRNLRRITR LVLVVVAVFV GCWTPVQVFV LVQGLGVQPG
SETAVAILRF CTALGYVNSC LNPILYAFLD

ENFKACFRKF CCASSLHREM QVSDRVRSIA KDVGLGCKTS ETVPRPA

FIG. 3A

```
              1                                                                          #  50
rXor1         ..........  ..........  ..........  .....MESLF  PAPYWEVLYG  SHFQGNLSLL
rMor1         MDSSTGPGNT  SDCSDPLAQA  SCSPAPGSWL  NLSHVDGNQS  DPCGLNRTGL
rDor1         ..........  ..........  ....MEPV    PSARAE...L  QFSLL.ANVS  DTFPSAFPSA
rKor1         ..........  ..MESPIQIF  RGEPGPTCAP  SACLLPN...S  SSWFPNWAES
Consensus     ----------  ----------  ----------  ----------S  ----------  ----------

#51                       #                                                100
rXor1         NETVPHHLLL  NASHSAFLPL  GLKVTIVGLY  LAVCIGGLLG  NCLVMYVILR
rMor1         GGNDSLCPQ.  ...TGSP.SM  VTAITIMALY  SIVCVVGLFG  NFLVMYVIVR
rDor1         SANASGSPG.  ...ARSASSL  ALAIAITALY  SAVCAVGLLG  NVLVMFGIVR
rKor1         DSNGSVGSED  QQLEPAHISP  AIPVIITAVY  SVVFVVGLVG  NSLVMFVIIR
Consensus     --N-S-----  -------S--  ---I-I-A-Y  S-V---VGL-G  N-LVMF-IVR 101                                                                         150
rXor1         HTKMKTATNI  YIFNLALADT  LVLLTLPFQG  TDILLGFWPF  GNALCKTVIA
rMor1         YTKMKTATNI  YIFNLALADA  LATSTLPFQS  VNYLMGTWPF  GTILCKIVIS
rDor1         YTKLKTATNI  YIFNLALADA  LATSTLPFQS  AKYLMETWPF  GELLCKAVLS
rKor1         YTKMKTATNI  YIFNLALADA  LVTTMPFQS   AVYLMNSWPF  GDVLCKIVIS
Consensus     -T-MKTATNI  YIFNLALADA  L-T-TLPFQS  --YLM--WPF  G---LCK-V-S
```

FIG. 3B

```
              151                                                   200
rXorl       IDYYNMFTST FTLTMSVDR YVAICHPIRA LDVRTSSKAQ AVNVAIWALA
rMorl       IDYYNMFTSI FTLCTMSVDR YIAVCHPVKA LDFRTPRNAK IVNVCNWILS
rDorl       IDYYNMFTSI FTLTMMSVDR YIAVCHPVKA LDFRTPAKAK LINICIWVLA
rKorl       IDYYNMFTSI FTLTMMSVDR YIAVCHPVKA LDFRTPLKAK IINICIWLLA
Consensus   IDYYNMFTSI FTL--MSVDR YIAVCHPVKA LDFRTP---AK -INIC-W-L-

GQWVVLLPDSLVSHGFLLVPLPPNPSPA
              201                                                   250
rXorl       SVVGVPVAIM GSAQVED...E EIECLVEIPA PQ.DYWGPVF AICIFLFSFI
rMorl       SAIGLPVMFM ATTKYRQ..G SIDCTLTFSH PTW.YWENLL KICVFIFAFI
rDorl       SGVGVPIMVM AVTQPRD..G AVVCTLQFPS PSW.YWDTVT KICVFLFAFV
rKorl       SSVGISAIVL GGTKVREDVD VIECSLQFPD DEYSWWDLFM KICVFVFAFV
Consensus   S-VG-----M --T---R---- --I-C-L-F-- --W-YWD--- KICVF-FAFV 251                                                   300
rXorl       IPVLIISVCY SLMIRRLRGV RLLSGSREKD RNLRRITRLV LVVVAVFVGC
rMorl       MPVLIITVCY GLMILRLKSV RMLSGSKEKD RNLRRITRMV LVVVAVFIVC
rDorl       VPILIITVCY GLMLLRLRSV RLLSGSKEKD RSLRRITRMV LVVVGAFVVC
rKorl       IPVLIIIVCY TLMILRLKSV RLLSGSREKD RNLRRITKLV LVVVAVFIIC
Consensus   -PVLII-VCY -LM-LRL-SV RLLSGS-EKD R-LRRIT-MV LVVV--FIVC
```

FIG. 3C

```
          301                                                          350
rXorl     WTPVQVFVLV QGL.GVQPGS ETAVAILRFC TALGYVNSCL NPILYAFLDE
rMorl     WTPIHIYVII KALITI.PET TFQTVSWHFC IALGYTNSCL NPVLYAFLDE
rDorl     WAPIHIFVIV WTLVDINRRD PLVVAALHLC IALGYANSSL NPVLYAFLDE
rKorl     WTPIHIFILV EALGSTSHST A.VLSSYYFC IALGYTNSSL NPVLYAFLDE
Consensus W-PIHIFV-V --L------ ---------- IALGY-NS-L NPVLYAFLDE 351                                                          400
rXorl     NFKACFRKFC LLSSLHREMQ VSDRVRSIAK DVGLGCKTSE TVPRPA....
rMorl     NFKRCFREFC IPTSSTIEQQ NSTRVRQNTR EHPSTANTVD RTNHQLENLE
rDorl     NFKRCFRQLC RAPCGGQEPG SLRRPRQATA RERVTACTPS .....DGPG
rKorl     NFKRCFRDFC FPIKMRMERQ STNRVR.NTV QDPASMRDVG GMNKPV....
Consensus NFKRCFR-FC ------E-- ---R--R--T- ---------- ----------
```

1 2 3 4 5 6 7 8 9 10 11 12 13 14 15 16

RNAS

1 = BRAIN
2 = PITUITARY
3 = $GH_4C_1$ CELLS
4 = THYMUS
5 = LUNG
6 = HEART
7 = LIVER
8 = KIDNEY
9 = SPLEEN
10 = STOMACH
11 = MUSCLE
12 = FAT
13 = OVARY
14 = TESTIS

CONTROLS

15 = GENOMIC DNA
16 = NO TEMPLATE 1 2 3 4 5 6 7 8 9 10 11 12 13 14 15 16 17 18 19

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:
( A ) LENGTH: 2706 base pairs
( B ) TYPE: nucleic acid
( C ) STRANDEDNESS: single
( D ) TOPOLOGY: linear ( i i ) MOLECULE TYPE: cDNA ( v i ) ORIGINAL SOURCE:
( F ) TISSUE TYPE: Rat brain ( x i ) SEQUENCE DESCRIPTION: SEQ ID NO:1:

```
GCGGCCGCCT TTCTGCTAAG CATTGGGGTC TATTTTGGCC CAGCTTCTGA AGAGGCTGTG        60
TGTGCCGTTG GAGGAACTGT ACTGAGTGGC TTTGCAGGGT GACAGCATGG AGTCCCTCTT       120
TCCTGCTCCA TACTGGGAGG TCTTGTATGG CAGCCACTTT CAAGGGAACC TGTCCCTCCT       180
AAATGAGACC GTACCCACC  ACCTGCTCCT CAATGCTAGT CACAGCGCCT TCCTGCCCCT       240
TGGACTCAAG GTCACCATCG TGGGGCTCTA CTTGGCTGTG TGCATCGGGG GGCTCCTGGG       300
GAACTGCCTC GTCATGTATG TCATCCTCAG GCACACCAAG ATGAAGACAG CTACCAACAT       360
TTACATATTT AATCTGGCAC TGGCTGATAC CCTGGTCTTG CTAACACTGC CCTTCCAGGG       420
CACAGACATC CTACTGGGCT TCTGGCCATT TGGGAATGCA CTCTGCAAGA CTGTCATTGC       480
TATCGACTAC TACAACATGT TTACCAGCAC TTTTACTCTG ACCGCCATGA GCGTAGACCG       540
CTATGTGGCT ATCTGCCACC CTATCCGTGC CCTTGATGTT CGGACATCCA GCAAAGCCCA       600
GGCTGTTAAT GTGGCCATAT GGGCCCTGGC TTCAGTGGTT GGTGTTCCTG TTGCCATCAT       660
GGGTTCAGCA CAAGTGGAAG ATGAAGAGAT CGAGTGCCTG GTGGAGATCC CTGCCCCTCA       720
GGACTATTGG GGCCCTGTAT TCGCCATCTG CATCTTCCTT TTTTCCTTCA TCATCCCTGT       780
GCTGATCATC TCTGTCTGCT ACAGCCTCAT GATTCGACGA CTTCGTGGTG TCCGTCTGCT       840
TTCAGGCTCC CGGGAGAAGG ACCGAAACCT GCGGCGTATC ACTCGACTGG TGCTGGTAGT       900
GGTGGCTGTG TTTGTGGGCT GCTGGACGCC TGTGCAGGTG TTTGTCCTGG TTCAAGGACT       960
GGGTGTTCAG CCAGGTAGTG AGACTGCAGT TGCCATCCTG CGCTTCTGCA CAGCCCTGGG      1020
CTATGTCAAC AGTTGTCTCA ATCCCATTCT CTATGCTTTC CTGGATGAGA ACTTCAAGGC      1080
CTGCTTTAGA AAGTTCTGCT GTGCTTCATC CCTGCACCGG GAGATGCAGG TTTCTGATCG      1140
TGTGCGGAGC ATTGCCAAGG ATGTTGGCCT TGGTTGCAAG ACTTCTGAGA CAGTACCACG      1200
GCCAGCATGA CTAGGCGTGG ACCTGCCCAT GGTGCCTGTC AGCCCACAGA GCCCATCTAC      1260
ACCCAACACG GAGCTCACAC AGGTCACTGC TCTCTAGGTT GACCCTGAAC CTTGAGCATC      1320
TGGAGCCTTG AATGGCTTTT CTTTTGGATC AGGATGCTCA GTCCTAGAGG AAGACCTTTT      1380
```

| | | | | | |
|---|---|---|---|---|---|
|AGCACCATGG|GACAGGTCAA|AGCATCAAGG|TGGTCTCCAT|GGCCTCTGTC|AGATTAAGTT|1440|
|CCCTCCCTGG|TATAGGACCA|GAGAGGACCA|AAGGAACTGA|ATAGAAACAT|CCACAACACA|1500|
|GTGGACATGC|CTGGTGAGCC|CATGTAGGTA|TTCATGCTTC|ACTTGACTCT|TCTCTGGCTT|1560|
|CTCCCTGCTG|CCCTGGCTCT|AGCTGGGCTC|AACCTGAGGT|ATTGTAGTGG|TCATGTAGTC|1620|
|ACTCTTGTGA|CTACATGTTG|TGTGCTGTTG|CTCTCGGCCT|TTCAGTATTT|CCACAGGACT|1680|
|GCTGAACATA|CCTGGTATTG|CAGTGGGGAG|CATTAATTTT|CTTTTAAAGT|GAGACTGGCC|1740|
|CTTAAGCTTG|GCGTTGCCTT|GGAGCGTCTT|CTACTTCTGA|CTTCACTGAT|GCAGTCAGAT|1800|
|TACCCGAGGG|TGAGCATCAG|TGGTTTCTTG|GATGGCTGTT|TTCTGAAGAT|TCTTCCCATC|1860|
|CAGTACATGG|AGTCTATGAA|GGGGAGTCAC|AATTCATCTG|GTACTGCCAC|TACCTGCTCT|1920|
|ATAATCCTGG|GCTATCTTCT|TGGCAAGATG|ACAGTGGGGG|AGACAAGACA|CAGAGCTTCC|1980|
|CTAAGGCTCT|TTCCCTCCAA|AACCACTGTG|AACTCTTATC|CTACAGACTG|TTCGGCAAGC|2040|
|ACTGCTTCTA|GGTGTGTGGG|AGGTAATCAG|GAGAAAGCTT|TGTGGCCTCT|GTAGGCTGCT|2100|
|CACAACATGG|AGGCACCACA|TGCTGGTCTT|GCCTGCTTAG|TACAGGCAGG|ACAGAGCAGA|2160|
|ATATGCTCTC|TCTCGATTCT|CTACAAACTC|CCTCAGTTCT|CCAGCAGAGT|CTCTTTTACT|2220|
|TGCTATCAGA|GGTCAGGAGT|TGTACTGCTA|GAAGCATACT|TGTAGCTTGG|AAGAGTGGC|2280|
|AGTCAGGATG|TGTTCTACTC|TATATCCACA|GTGACCACCT|GCTTCATATA|TAGGGTTAGG|2340|
|ACATATCTGA|GTAAGGCCTG|AGTGTGCTGC|CAAATTGGAG|GTTGGTATGA|GAGCTGATGC|2400|
|CTAAAGTGGC|TCATTTGCAA|GGACTATTAT|GGTTTGGAAT|AGCAATGGGG|GGCATGGGAA|2460|
|GAAGAGTCTA|TACCTTGGAG|ATCTATTTGA|TGGTTCACAG|AAGAGGTTTT|GTAAACGCCC|2520|
|TTTCTATGGG|TCAGATATCA|AAATACCAGC|AACGTTGGAT|AGATTCTGAC|CTTTTACTGA|2580|
|GACCTCGGTC|AGATGGTTTC|ATGTCATGCA|GAGAACCTAG|GCTGGTTCCT|GTGTCAGAGA|2640|
|GACCTGGGCT|TCTGGGAGG|CCAGGGTTCT|TCCTTTGACA|CTTGTGCGGG|AGCCGTTAGC|2700|
|TCTAGA| | | | | |2706|

( 2 ) INFORMATION FOR SEQ ID NO:2:

( i ) SEQUENCE CHARACTERISTICS:
        ( A ) LENGTH: 367 amino acids
        ( B ) TYPE: amino acid
        ( C ) STRANDEDNESS: Not Relevant
        ( D ) TOPOLOGY: Not Relevant ( i i ) MOLECULE TYPE: protein ( v i ) ORIGINAL SOURCE:
        ( A ) ORGANISM: Rat ( x i ) SEQUENCE DESCRIPTION: SEQ ID NO:2:

```
Met   Glu   Ser   Leu   Phe   Pro   Ala   Pro   Tyr   Trp   Glu   Val   Leu   Tyr   Gly   Ser
  1                 5                            10                          15

His   Phe   Gln   Gly   Asn   Leu   Ser   Leu   Leu   Asn   Glu   Thr   Val   Pro   His   His
                    20                            25                          30

Leu   Leu   Leu   Asn   Ala   Ser   His   Ser   Ala   Phe   Leu   Pro   Gly   Leu   Lys
              35                            40                          45

Val   Thr   Ile   Val   Gly   Leu   Tyr   Leu   Ala   Val   Cys   Ile   Gly   Gly   Leu   Leu
        50                            55                          60

Gly   Asn   Cys   Leu   Val   Met   Tyr   Val   Ile   Leu   Arg   His   Thr   Lys   Met   Lys
 65                            70                          75                          80

Thr   Ala   Thr   Asn   Ile   Tyr   Ile   Phe   Asn   Leu   Ala   Leu   Ala   Asp   Thr   Leu
                    85                            90                          95
```

| | | | | | | | | | | | | | | |
|---|---|---|---|---|---|---|---|---|---|---|---|---|---|---|
| Val | Leu | Leu | Thr<br>100 | Leu | Pro | Phe | Gln | Gly<br>105 | Thr | Asp | Ile | Leu<br>110 | Leu | Gly | Phe |
| Trp | Pro | Phe<br>115 | Gly | Asn | Ala | Leu | Cys<br>120 | Lys | Thr | Val | Ile | Ala<br>125 | Ile | Asp | Tyr |
| Tyr | Asn<br>130 | Met | Phe | Thr | Ser | Thr<br>135 | Phe | Thr | Leu | Thr | Ala<br>140 | Met | Ser | Val | Asp |
| Arg<br>145 | Tyr | Val | Ala | Ile | Cys<br>150 | His | Pro | Ile | Arg | Ala<br>155 | Leu | Asp | Val | Arg | Thr<br>160 |
| Ser | Ser | Lys | Ala | Gln<br>165 | Ala | Val | Asn | Val | Ala<br>170 | Ile | Trp | Ala | Leu | Ala<br>175 | Ser |
| Val | Val | Gly | Val<br>180 | Pro | Val | Ala | Ile | Met<br>185 | Gly | Ser | Ala | Gln | Val<br>190 | Glu | Asp |
| Glu | Glu | Ile | Glu<br>195 | Cys | Leu | Val | Glu<br>200 | Ile | Pro | Ala | Pro | Gln<br>205 | Asp | Tyr | Trp |
| Gly | Pro | Val<br>210 | Phe | Ala | Ile | Cys<br>215 | Ile | Phe | Leu | Phe | Ser<br>220 | Phe | Ile | Ile | Pro |
| Val<br>225 | Leu | Ile | Ile | Ser | Val<br>230 | Cys | Tyr | Ser | Leu | Met<br>235 | Ile | Arg | Arg | Leu | Arg<br>240 |
| Gly | Val | Arg | Leu | Leu<br>245 | Ser | Gly | Ser | Arg | Glu<br>250 | Lys | Asp | Arg | Asn | Leu<br>255 | Arg |
| Arg | Ile | Thr | Arg<br>260 | Leu | Val | Leu | Val | Val<br>265 | Ala | Val | Phe | Val<br>270 | Gly | Cys |
| Trp | Thr | Pro<br>275 | Val | Gln | Val | Phe | Val<br>280 | Leu | Val | Gln | Gly | Leu<br>285 | Gly | Val | Gln |
| Pro | Gly<br>290 | Ser | Glu | Thr | Ala | Val<br>295 | Ala | Ile | Leu | Arg | Phe<br>300 | Cys | Thr | Ala | Leu |
| Gly<br>305 | Tyr | Val | Asn | Ser | Cys<br>310 | Leu | Asn | Pro | Ile | Leu<br>315 | Tyr | Ala | Phe | Leu | Asp<br>320 |
| Glu | Asn | Phe | Lys | Ala<br>325 | Cys | Phe | Arg | Lys | Phe<br>330 | Cys | Cys | Ala | Ser | Ser<br>335 | Leu |
| His | Arg | Glu | Met<br>340 | Gln | Val | Ser | Asp | Arg<br>345 | Val | Arg | Ser | Ile | Ala<br>350 | Lys | Asp |
| Val | Gly | Leu<br>355 | Gly | Cys | Lys | Thr | Ser<br>360 | Glu | Thr | Val | Pro | Arg<br>365 | Pro | Ala | |

(2) INFORMATION FOR SEQ ID NO:3:

(i) SEQUENCE CHARACTERISTICS:
        (A) LENGTH: 391 amino acids
        (B) TYPE: amino acid
        (C) STRANDEDNESS: Not Relevant
        (D) TOPOLOGY: Not Relevant (ii) MOLECULE TYPE: protein (vi) ORIGINAL SOURCE:
        (A) ORGANISM: Rat (xi) SEQUENCE DESCRIPTION: SEQ ID NO:3:

| | | | | | | | | | | | | | | |
|---|---|---|---|---|---|---|---|---|---|---|---|---|---|---|
| Met<br>1 | Asp | Ser | Ser | Thr<br>5 | Gly | Pro | Gly | Asn | Thr<br>10 | Ser | Asp | Cys | Ser | Asp<br>15 | Pro |
| Leu | Ala | Gln | Ala<br>20 | Ser | Cys | Ser | Pro | Ala<br>25 | Pro | Gly | Ser | Trp | Leu<br>30 | Asn | Leu |
| Ser | His | Val<br>35 | Asp | Gly | Asn | Gln | Ser<br>40 | Asp | Pro | Cys | Gly | Leu<br>45 | Asn | Arg | Thr |
| Gly | Leu<br>50 | Gly | Gly | Asn | Asp | Ser<br>55 | Leu | Cys | Pro | Gln | Thr<br>60 | Gly | Ser | Pro | Ser |

| Met | Val | Thr | Ala | Ile | Thr | Ile | Met | Ala | Leu | Tyr | Ser | Ile | Val | Cys | Val |
| 65 | | | | 70 | | | | | 75 | | | | | | 80 |

| Val | Gly | Leu | Phe | Gly | Asn | Phe | Leu | Val | Met | Tyr | Val | Ile | Val | Arg | Tyr |
| | | | | 85 | | | | | 90 | | | | | 95 | |

| Thr | Lys | Met | Lys | Thr | Ala | Thr | Asn | Ile | Tyr | Ile | Phe | Asn | Leu | Ala | Leu |
| | | | 100 | | | | | 105 | | | | | 110 | | |

| Ala | Asp | Ala | Leu | Ala | Thr | Ser | Thr | Leu | Pro | Phe | Gln | Ser | Val | Asn | Tyr |
| | | | 115 | | | | 120 | | | | | 125 | | | |

| Leu | Met | Gly | Thr | Trp | Pro | Phe | Gly | Thr | Ile | Leu | Cys | Lys | Ile | Val | Ile |
| | | 130 | | | | 135 | | | | | 140 | | | | |

| Ser | Ile | Asp | Tyr | Tyr | Asn | Met | Phe | Thr | Ser | Ile | Phe | Thr | Leu | Cys | Thr |
| 145 | | | | | 150 | | | | | 155 | | | | | 160 |

| Met | Ser | Val | Asp | Arg | Tyr | Ile | Ala | Val | Cys | His | Pro | Val | Lys | Ala | Leu |
| | | | | 165 | | | | | 170 | | | | | 175 | |

| Asp | Phe | Arg | Thr | Pro | Arg | Asn | Ala | Lys | Ile | Val | Asn | Val | Cys | Asn | Trp |
| | | | 180 | | | | | 185 | | | | | 190 | | |

| Ile | Leu | Ser | Ser | Ala | Ile | Gly | Leu | Pro | Val | Met | Phe | Met | Ala | Thr | Thr |
| | | | 195 | | | | | 200 | | | | | 205 | | |

| Lys | Tyr | Arg | Gln | Gly | Ser | Ile | Asp | Cys | Thr | Leu | Thr | Phe | Ser | His | Pro |
| | | 210 | | | | | 215 | | | | 220 | | | | |

| Thr | Trp | Tyr | Trp | Glu | Asn | Leu | Leu | Lys | Ile | Cys | Val | Phe | Ile | Phe | Ala |
| 225 | | | | | 230 | | | | | 235 | | | | | 240 |

| Phe | Ile | Met | Pro | Val | Leu | Ile | Ile | Thr | Val | Cys | Tyr | Gly | Leu | Met | Ile |
| | | | | 245 | | | | | 250 | | | | | 255 | |

| Leu | Arg | Leu | Lys | Ser | Val | Arg | Met | Leu | Ser | Gly | Ser | Lys | Glu | Lys | Asp |
| | | | 260 | | | | | 265 | | | | | 270 | | |

| Arg | Asn | Leu | Arg | Arg | Ile | Thr | Arg | Met | Val | Leu | Val | Val | Val | Ala | Val |
| | | 275 | | | | | 280 | | | | | 285 | | | |

| Phe | Ile | Val | Cys | Trp | Thr | Pro | Ile | His | Ile | Tyr | Val | Ile | Ile | Lys | Ala |
| | | 290 | | | | | 295 | | | | | 300 | | | |

| Leu | Ile | Thr | Ile | Pro | Glu | Thr | Thr | Phe | Gln | Thr | Val | Ser | Trp | His | Phe |
| 305 | | | | | 310 | | | | | 315 | | | | | 320 |

| Cys | Ile | Ala | Leu | Gly | Tyr | Thr | Asn | Ser | Cys | Leu | Asn | Pro | Val | Leu | Tyr |
| | | | | 325 | | | | | 330 | | | | | 335 | |

| Ala | Phe | Leu | Asp | Glu | Asn | Phe | Lys | Arg | Cys | Phe | Arg | Glu | Phe | Cys | Ile |
| | | | 340 | | | | | 345 | | | | | 350 | | |

| Pro | Thr | Ser | Ser | Thr | Ile | Glu | Gln | Gln | Asn | Ser | Thr | Arg | Val | Arg | Gln |
| | | | 355 | | | | | 360 | | | | | 365 | | |

| Asn | Thr | Arg | Glu | His | Pro | Ser | Thr | Ala | Asn | Thr | Val | Asp | Arg | Thr | Asn |
| | | 370 | | | | | 375 | | | | | 380 | | | |

| His | Gln | Leu | Glu | Asn | Leu | Glu |
| 385 | | | | | 390 | |

( 2 ) INFORMATION FOR SEQ ID NO:4:

( i ) SEQUENCE CHARACTERISTICS:
        ( A ) LENGTH: 367 amino acids
        ( B ) TYPE: amino acid
        ( C ) STRANDEDNESS: Not Relevant
        ( D ) TOPOLOGY: Not Relevant ( i i ) MOLECULE TYPE: protein ( v i ) ORIGINAL SOURCE:
        ( A ) ORGANISM: Rat ( x i ) SEQUENCE DESCRIPTION: SEQ ID NO:4:

| Met | Glu | Pro | Val | Pro | Ser | Ala | Arg | Ala | Glu | Leu | Gln | Phe | Ser | Leu | Leu |

```
            1                     5                    10                    15

Ala  Asn  Val  Ser  Asp  Thr  Phe  Pro  Ser  Ala  Phe  Pro  Ser  Ala  Ser  Ala
                           20                  25                 30

Asn  Ala  Ser  Gly  Ser  Pro  Gly  Ala  Arg  Ser  Ala  Ser  Ser  Leu  Ala  Leu
                      35                  40                 45

Ala  Ile  Ala  Ile  Thr  Ala  Leu  Tyr  Ser  Ala  Val  Cys  Ala  Val  Gly  Leu
                 50                  55                 60

Leu  Gly  Asn  Val  Leu  Val  Met  Phe  Gly  Ile  Val  Arg  Tyr  Thr  Lys  Leu
            65                  70                  75                               80

Lys  Thr  Ala  Thr  Asn  Ile  Tyr  Ile  Phe  Asn  Leu  Ala  Leu  Ala  Asp  Ala
                                85                  90                            95

Leu  Ala  Thr  Ser  Thr  Leu  Pro  Phe  Gln  Ser  Ala  Lys  Tyr  Leu  Met  Glu
                           100                 105                      110

Thr  Trp  Pro  Phe  Gly  Glu  Leu  Leu  Cys  Lys  Ala  Val  Leu  Ser  Ile  Asp
                           115                 120                      125

Tyr  Tyr  Asn  Met  Phe  Thr  Ser  Ile  Phe  Thr  Leu  Thr  Met  Met  Ser  Val
                 130                      135                 140

Asp  Arg  Tyr  Ile  Ala  Val  Cys  His  Pro  Val  Lys  Ala  Leu  Asp  Phe  Arg
            145                      150                      155                      160

Thr  Pro  Ala  Lys  Ala  Lys  Leu  Ile  Asn  Ile  Cys  Ile  Trp  Val  Leu  Ala
                                165                      170                      175

Ser  Gly  Val  Gly  Val  Pro  Ile  Met  Val  Met  Ala  Val  Thr  Gln  Pro  Arg
                           180                      185                      190

Asp  Gly  Ala  Val  Val  Cys  Thr  Leu  Gln  Phe  Pro  Ser  Pro  Ser  Trp  Tyr
                      195                      200                 205

Trp  Asp  Thr  Val  Thr  Lys  Ile  Cys  Val  Phe  Leu  Phe  Ala  Phe  Val  Val
                 210                      215                      220

Pro  Ile  Leu  Ile  Ile  Thr  Val  Cys  Tyr  Gly  Leu  Met  Leu  Leu  Arg  Leu
            225                           230                 235                      240

Arg  Ser  Val  Arg  Leu  Leu  Ser  Gly  Ser  Lys  Glu  Lys  Asp  Arg  Ser  Leu
                                245                      250                      255

Arg  Arg  Ile  Thr  Arg  Met  Val  Leu  Val  Val  Val  Gly  Ala  Phe  Val  Val
                           260                      265                      270

Cys  Trp  Ala  Pro  Ile  His  Ile  Phe  Val  Ile  Val  Trp  Thr  Leu  Val  Asp
                      275                      280                 285

Ile  Asn  Arg  Arg  Asp  Pro  Leu  Val  Val  Ala  Ala  Leu  His  Leu  Cys  Ile
                 290                      295                 300

Ala  Leu  Gly  Tyr  Ala  Asn  Ser  Ser  Leu  Asn  Pro  Val  Leu  Tyr  Ala  Phe
            305                      310                      315                      320

Leu  Asp  Glu  Asn  Phe  Lys  Arg  Cys  Phe  Arg  Gln  Leu  Cys  Arg  Ala  Pro
                                325                      330                      335

Cys  Gly  Gly  Gln  Glu  Pro  Gly  Ser  Leu  Arg  Arg  Pro  Arg  Gln  Ala  Thr
                           340                      345                      350

Ala  Arg  Glu  Arg  Val  Thr  Ala  Cys  Thr  Pro  Ser  Asp  Gly  Pro  Gly
                      355                      360                      365
```

( 2 ) INFORMATION FOR SEQ ID NO:5:

( i ) SEQUENCE CHARACTERISTICS:
        ( A ) LENGTH: 330 amino acids
        ( B ) TYPE: amino acid
        ( C ) STRANDEDNESS: Not Relevant
        ( D ) TOPOLOGY: Not Relevant ( i i ) MOLECULE TYPE: protein ( v i ) ORIGINAL SOURCE:

(A) ORGANISM: Rat (xi) SEQUENCE DESCRIPTION: SEQ ID NO:5:

| Met | Glu | Ser | Pro | Ile | Gln | Ile | Phe | Arg | Gly | Glu | Pro | Gly | Pro | Thr | Cys |
|---|---|---|---|---|---|---|---|---|---|---|---|---|---|---|---|
| 1 | | | | 5 | | | | | 10 | | | | | 15 | |
| Ala | Pro | Ser | Ala | Cys | Leu | Leu | Pro | Asn | Ser | Ser | Ser | Trp | Phe | Pro | Asn |
| | | | 20 | | | | 25 | | | | | | 30 | | |
| Trp | Ala | Glu | Ser | Asp | Ser | Asn | Gly | Ser | Val | Gly | Ser | Glu | Asp | Gln | Gln |
| | | 35 | | | | | 40 | | | | | 45 | | | |
| Leu | Glu | Pro | Ala | His | Ile | Ser | Pro | Ala | Ile | Pro | Val | Ile | Ile | Thr | Ala |
| | 50 | | | | | 55 | | | | | 60 | | | | |
| Val | Tyr | Ser | Val | Val | Phe | Val | Val | Gly | Leu | Val | Gly | Asn | Ser | Leu | Val |
| 65 | | | | | 70 | | | | | 75 | | | | | 80 |
| Met | Phe | Val | Ile | Ile | Arg | Tyr | Thr | Lys | Met | Lys | Thr | Ala | Thr | Asn | Ile |
| | | | | 85 | | | | | 90 | | | | | 95 | |
| Tyr | Ile | Phe | Asn | Leu | Ala | Leu | Ala | Asp | Ala | Leu | Val | Thr | Thr | Thr | Met |
| | | | 100 | | | | | 105 | | | | | 110 | | |
| Pro | Phe | Gln | Ser | Ala | Val | Tyr | Leu | Met | Asn | Ser | Trp | Pro | Phe | Gly | Asp |
| | | 115 | | | | | 120 | | | | | 125 | | | |
| Val | Leu | Cys | Lys | Ile | Val | Ile | Ser | Ser | Ser | Val | Gly | Ile | Ser | Ala | Ile |
| | 130 | | | | | 135 | | | | | 140 | | | | |
| Val | Leu | Gly | Gly | Thr | Lys | Val | Arg | Glu | Asp | Val | Asp | Val | Ile | Glu | Cys |
| 145 | | | | | 150 | | | | | 155 | | | | | 160 |
| Ser | Leu | Gln | Phe | Pro | Asp | Asp | Glu | Tyr | Ser | Trp | Trp | Asp | Leu | Phe | Met |
| | | | | 165 | | | | | 170 | | | | | 175 | |
| Lys | Ile | Cys | Val | Phe | Val | Phe | Ala | Phe | Val | Ile | Pro | Val | Leu | Ile | Ile |
| | | | 180 | | | | | 185 | | | | | 190 | | |
| Ile | Val | Cys | Tyr | Thr | Leu | Met | Ile | Leu | Arg | Leu | Lys | Ser | Val | Arg | Leu |
| | | 195 | | | | | 200 | | | | | 205 | | | |
| Leu | Ser | Gly | Ser | Arg | Glu | Lys | Asp | Arg | Asn | Leu | Arg | Arg | Ile | Thr | Lys |
| | 210 | | | | | 215 | | | | | 220 | | | | |
| Leu | Val | Leu | Val | Val | Val | Ala | Val | Phe | Ile | Ile | Cys | Trp | Thr | Pro | Ile |
| 225 | | | | | 230 | | | | | 235 | | | | | 240 |
| His | Ile | Phe | Ile | Leu | Val | Glu | Ala | Leu | Gly | Ser | Thr | Ser | His | Ser | Thr |
| | | | | 245 | | | | | 250 | | | | | 255 | |
| Ala | Val | Leu | Ser | Ser | Tyr | Tyr | Phe | Cys | Ile | Ala | Leu | Gly | Tyr | Thr | Asn |
| | | | 260 | | | | | 265 | | | | | 270 | | |
| Ser | Ser | Leu | Asn | Pro | Val | Leu | Tyr | Ala | Phe | Leu | Asp | Glu | Asn | Phe | Lys |
| | | 275 | | | | | 280 | | | | | 285 | | | |
| Arg | Cys | Phe | Arg | Asp | Phe | Cys | Phe | Pro | Ile | Lys | Met | Arg | Met | Glu | Arg |
| | 290 | | | | | 295 | | | | | 300 | | | | |
| Gln | Ser | Thr | Asn | Arg | Val | Arg | Asn | Thr | Val | Gln | Asp | Pro | Ala | Ser | Met |
| 305 | | | | | 310 | | | | | 315 | | | | | 320 |
| Arg | Asp | Val | Gly | Gly | Met | Asn | Lys | Pro | Val | | | | | | |
| | | | | 325 | | | | | 330 | | | | | | |

(2) INFORMATION FOR SEQ ID NO:6:

(i) SEQUENCE CHARACTERISTICS:
        (A) LENGTH: 28 amino acids
        (B) TYPE: amino acid
        (C) STRANDEDNESS: Not Relevant
        (D) TOPOLOGY: Not Relevant (ii) MOLECULE TYPE: peptide (v) FRAGMENT TYPE: internal fragment (v i) ORIGINAL SOURCE:
(A) ORGANISM: Rat (x i) SEQUENCE DESCRIPTION: SEQ ID NO:6:

Gly Gln Trp Val Val Leu Leu Pro Asp Ser Leu Val Ser His Gly Phe
1               5                   10                  15

Leu Leu Val Pro Leu Pro Pro Asn Pro Ser Pro Ala
            20              25

(2) INFORMATION FOR SEQ ID NO:7:

(i) SEQUENCE CHARACTERISTICS:
(A) LENGTH: 25 base pairs
(B) TYPE: nucleic acid
(C) STRANDEDNESS: single
(D) TOPOLOGY: linear (i i) MOLECULE TYPE: other nucleic acid
(A) DESCRIPTION: /desc = "PCR PRIMER"

(x i) SEQUENCE DESCRIPTION: SEQ ID NO:7:

ACGATGAAGC ACTGAGCCAC CACCA 25

(2) INFORMATION FOR SEQ ID NO:8:

(i) SEQUENCE CHARACTERISTICS:
(A) LENGTH: 10 amino acids
(B) TYPE: amino acid
(C) STRANDEDNESS: Not Relevant
(D) TOPOLOGY: linear (i i) MOLECULE TYPE: peptide (v) FRAGMENT TYPE: internal (v i) ORIGINAL SOURCE:
(F) TISSUE TYPE: rat brain (x i) SEQUENCE DESCRIPTION: SEQ ID NO:8:

Val Leu Val Val Val Ala Val Phe Ile Val
1               5                   10

(2) INFORMATION FOR SEQ ID NO:9:

(i) SEQUENCE CHARACTERISTICS:
(A) LENGTH: 24 base pairs
(B) TYPE: nucleic acid
(C) STRANDEDNESS: single
(D) TOPOLOGY: linear (i i) MOLECULE TYPE: other nucleic acid
(A) DESCRIPTION: /desc = "PCR PRIMER"

(x i) SEQUENCE DESCRIPTION: SEQ ID NO:9:

CTTCAATCCT GGCTCTTGCC TGAT 24

(2) INFORMATION FOR SEQ ID NO:10:

(i) SEQUENCE CHARACTERISTICS:
(A) LENGTH: 21 base pairs
(B) TYPE: nucleic acid
(C) STRANDEDNESS: single
(D) TOPOLOGY: linear (i i) MOLECULE TYPE: other nucleic acid
(A) DESCRIPTION: /desc = "PCR PRIMER corresponding to
nucleotides 51 to 71 of SEQ ID NO:1"

(x i) SEQUENCE DESCRIPTION: SEQ ID NO:10:

AGGGCACAGA CATCCTACTG G 21

( 2 ) INFORMATION FOR SEQ ID NO:11:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "PCR PRIMER corresponding to
      nucleotides 546-566 of SEQ ID NO:1"

( x i ) SEQUENCE DESCRIPTION: SEQ ID NO:11:

AGCCTGAAAG CAGACGGACA C                                                         2 1

( 2 ) INFORMATION FOR SEQ ID NO:12:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "PCR PRIMER"

( x i ) SEQUENCE DESCRIPTION: SEQ ID NO:12:

ACCCTGGTCT TGCTAACA                                                             1 8

( 2 ) INFORMATION FOR SEQ ID NO:13:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "PCR PRIMER"

( x i ) SEQUENCE DESCRIPTION: SEQ ID NO:13:

CAGCACCAGT CGAGTGAT                                                             1 8

METHOD OF DETECTING EXPRESSION OF PROTEINS CLOSELY RELATED TO OPIOID RECEPTORS

This application is a divisional application of International Application No. PCT/US95/00939, filed Jan. 20, 1995, which is a continuation-in-part of U.S. patent application Ser. No. 08/185,360, filed Jan. 21, 1994, now abandoned.

1. Field of the Invention

This invention pertains to DNA sequences that encode opiorph receptor polypeptide(s). Opiorph receptor polypeptides are highly related to known opioid receptors. The invention also encompasses the opiorph receptors and antibodies directed against these polypeptides.

2. Background to the Invention

Opioid receptors are members of the receptor superfamily of polypeptides that typically have seven transmembrane domains and that are functionally coupled to G proteins. cDNAs encoding several types of opioid receptors have been cloned, including the mu, delta, and kappa opioid receptors (Wang et al., (1983), *Proc. Natl. Acad. Sci., USA,* 90:10230; Chen et al., (1993), *Mol. Pharmacol.,* 44:8; Evans et al., (1992), Science, 258:1952; Kieffer et al., *Proc. Natl. Acad. Sci., USA,* 89:12048; Yasuda et al, (1993), *Proc. Natl. Acad. Sci., USA,* 90:6736.)

It is believed that the proteins encoded by these cDNAs mediate many of the physiological effects of endogenous opioid agonist peptides, such as, for example, met- and leu-enkephalin, beta-endorphin, and dynorphin, as well as opiate alkaloids such as morphine (Jaffe and Martin, in *The Pharmacological Basis of Therapeutics,* A. G. Gilman et al., eds., MacMillan, New York, 1985, pages 491–531). These physiological effects, which occur in both the central and peripheral nervous system, include analgesia, drowsiness, mood changes, respiratory depression, decreased gastrointestinal mobility, nausea, vomiting, and other alterations in the endocrine and autonomic nervous system.

Another family of opioid receptors, the epsilon receptors, have been studied in brain and immune tissue (Nock et al., (1993), *J. Pharm. Expl. Therap.,* 264:349; Sibinga et al., (1988), *Ann. Rev. ImmunoL,* 6:219). Epsilon receptors, in the immune system, appear to mediate the effects of beta-endorphin on the cytotoxicity of monocytes, on conversion of precursor cells into killer cells, and on chemotaxis.

It has been found that some opioid effects may be mediated by receptors other than the known mu, delta, and kappa receptors. This indicates the existence of subtypes of each of these receptor classes. For example, two subtypes of mu-receptor, two subtypes of delta receptor, and three subtypes of kappa receptor have been identified pharmacologically (Pasternak, *Clin.Neuropharm.* 16:1, 1993).

New opioid receptor polypeptides have now been identified by isolating cDNAs that are homologous to known receptors.

BRIEF DESCRIPTION OF THE DRAWINGS

FIG. 1 is an illustration of DNA sequences encoding rat opiorph receptor polypeptides (SEQ ID NO:1).

FIG. 2 is an illustration of the predicted amino acid sequences of rat opiorph receptor polypeptides (SEQ ID NO:2).

FIG. 3 illustrates a comparison among an opiorph receptor polypeptide sequence of FIG. 2 (OR7) (rXor1) (SEQ ID NO:2) and the amino acid sequences of rat delta opioid receptor polypeptide (rDor1), (SEQ ID NO:4)rat mu opioid receptor polypeptide (rMor1) (SEQ ID NO:3), and rat kappa opioid receptor polypeptide (rKor1) (SEQ ID NO:5). Putative transmembrane domains are shaded. The extra amino acids encoded by the large splice variant of the opiorph receptor polypeptides are shown as an insert (SEQ ID NO:6).

SUMMARY OF THE INVENTION

Figure 4:
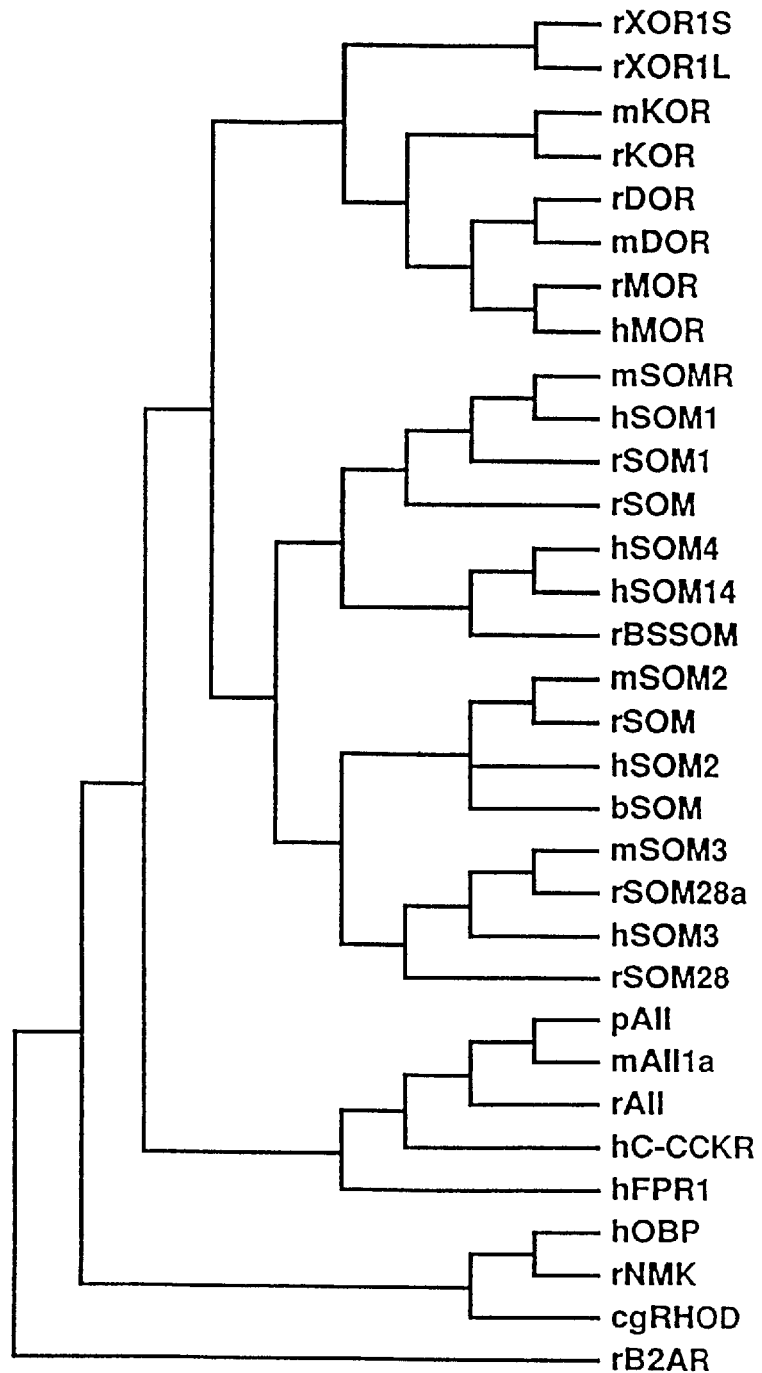
FIG. 4 is a dendrogram illustrating the evolutionary relatedness of the opiorph receptor polypeptides of FIG. 2 and other G-protein-linked receptor polypeptides.

Isolated DNAs encoding opiorph receptor polypeptides are provided. These DNAs include:

(A) nucleotides 367–918 of the DNA sequence of FIG. 1; (SEQ ID NO:1)

(B) nucleotides 368–916 of the DNA sequence of FIG. 1; (SEQ ID NO:1)

(C) DNA encoding amino acid residues 88–269 of the amino acid sequence of FIG. 2; (SEQ ID NO:2)

(D) sequence-conservative variants, function-conservative variants, and sequence- and function-conservative variants of any of (A), (B), or (C);

(E) intronless DNA encoding an amino acid sequence selected from the group consisting of amino acid residues 88–269 of the amino acid sequence of FIG. 2 (SEQ ID NO:2) and function-conservative variants thereof; and (F) DNA wherein exons of the DNA encode an amino acid sequence selected from the group consisting of amino acid residues 88–269 of the amino acid sequence of FIG. (SEQ ID NO:2) 2 and function-conservative variants thereof.

Recombinant cloning vectors comprising these DNA sequences and cells comprising these vectors are provided as well.

Also contemplated by the present invention are methods for detecting the expression, in a tissue, of MRNA encoding a polypeptide having an amino acid sequence selected from the group consisting of amino acid residues 88–269 of the amino acid sequence of FIG. 2 (SEQ ID NO:2) and function-conservative variants thereof. These methods comprise:

(A) selecting at least one oligonucleotide sequence unique to the polypeptide, wherein the sequence comprises from about 15 to about 30 nucleotides;

(B) synthesizing the oligonucleotides;

(C) hybridizing the oligonucleotide to total MRNA isolated from the tissue under stringent conditions; and (D) detecting the hybridization.

Further contemplated are methods for producing a polypeptide selected form the group consisting of amino acid residues 88–269 of the amino acid sequence of FIG. 2 SEQ ID NO:2 and function-conservative variants thereof. These methods include (A) culturing the cells above in a medium and under conditions suitable for expression of the polypeptide;

(B) expressing the polypeptide; and (C) optionally, isolating the expressed polypeptide.

Isolated polypeptides selected from the group consisting of amino acid residues 88–269 of FIG. 2 (SEQ ID NO:2) and function-conservative variants thereof, as well as antibodies to these polypeptides are also contemplated.

DETAILED DESCRIPTION OF THE INVENTION

DNA has been isolated that encodes opiorph receptor polypeptide(s). These opiorph receptor polypeptide(s) are related to, but distinct from, known opioid receptor polypeptides. The opiorph receptor polypeptide(s) has been characterized, establishing the differences between it and other members of the opioid receptor family. Accordingly, the opiorph receptor polypeptide(s) is an important target for the development of new opioid or opioid-like agonists and antagonists, which are psychotropic, analgesic, anti-emetic, immunomodulatory, growth hormone-releasing, and growth-promoting agents. Agonists or antagonists of the invertebrate homologue(s) of the opiorph receptor polypeptide(s) are believed to be pesticides. The DNA, opiorph receptor polypeptide(s), and antibodies of the present invention can be used, for example, for the detection and manipulation of pharmacological phenomena that are mediated by opioids and opioid-related molecules.

Opiorph Receptor Nucleic Acids

The DNA sequence set forth in FIG. 1 (SEQ ID NO:1) corresponds to the cDNA sequence encoding the seven transmembrane domain opiorph receptor polypeptide (OR7). The 3.2 kb sequence comprises a 5' untranslated region of 128 bp, an open reading frame of 1,101 bp, and a 3' untranslated region of 2 kb that includes a polyadenylation consensus site. The sequence also includes a splice donor site and a splice acceptor site. When the intervening sequence is excised by splicing, the resulting sequence encodes a smaller form of opiorph receptor polypeptide. The sequence between nucleotides 367 and 918 and preferably between nucleotides 368 and 916 encodes a five transmembrane-domain polypeptide (OR-5) (amino acid residues 88–269 of FIG. 2) (SEQ ID NO:2).

FIG. 2 (SEQ ID NO:2) illustrates the amino acid sequence of the opiorph receptor polypeptides OR5 and OR7 including a long splice variant (OR7L) and a short splice variant (OR7S), i.e. the polypeptide encoded by the DNA sequence of FIG. 1(SEQ ID NO:1). Because of the degeneracy of the genetic code in that multiple codons encode for certain amino acids, DNA sequences other than that shown in FIG. 1 (SEQ ID NO:1) can also encode the opiorph amino acid sequences shown in FIG. 2(SEQ ID NO:2). Such other DNAs include those containing "sequence-conservative" variation in which a change in one or more nucleotides in a given codon results in no alteration in the amino acid encoded at that position.

Additionally, a given amino acid residue in a polypeptide can be changed without altering the overall conformation and function of the native polypeptide. Such "function-conservative" varants include, but are not limited to, replacement of an amino acid with one having similar physico-chemical properties, such as, for example, acidic, basic, hydrophobic, and the like.

The opiorph receptor(s) DNAs within the scope of the present invention are those of FIG. 1(SEQ ID NO:1), sequence-conservative variant DNAs, DNA sequences encoding function-conservative variant polypeptides, and combinations thereof.

Generally, nucleic acid manipulations according to the present invention use methods that are well known in the art, as disclosed in e.g. *Molecular Cloning, A Laboratory Manual* (2nd Ed., Sambrook, Fritsch and Maniatis, Cold Spring Harbor), or *Current Protocols in Molecular Biology* (Eds. Aufubel, Brent, Kingston, More, Feidman, Smith and Stuhl, Greene Publ. Assoc., Wiley-Interscience, NY, N.Y., 1992).

The present invention encompasses cDNA and RNA sequences and sense and antisense sequences. The invention also encompasses genomic opiorph receptor polypeptide DNA sequences and flanking sequences, including, but not limited to, regulatory sequences. Nucleic acid sequences encoding opiorph receptor polypeptide(s) may also be associated with heterologous sequences, including promoters, enhancers, response elements, signal sequences, polyadenylation sequences, introns, 5'- and 3'- noncoding regions, and the like. Transcriptional regulatory elements that may be operably linked to opioiph receptor polypeptide DNA sequence(s) include, without limitation, those that have the ability to direct the expression of genes derived from prokaryotic cells, eukaryotic cells, viruses of prokaryotic cells, viruses of eukaryotic cells, and any combination thereof. Other useful heterologous sequences are known to those skilled in the art.

The nucleic acids of the present invention can be modified by methods known to those skilled in the art to alter their stability, solubility, binding affinity, and specificity. For example, the sequences can be selectively methylated. The nucleic acid sequences of the present invention may also be modified with a label capable of providing a detectable signal, either directly or indirectly. Exemplary labels include radioisotopes, fluorescent molecules, biotin, and the like.

Vectors and Transformants

The present invention also provides vectors that include nucleic acids encoding the opiorph receptor polypeptide(s). Such vectors include, for example, plasmid vectors for expression in a variety of eukaryotic and prokaryotic hosts. Preferably, vectors also include a promotor operably linked to the opiorph receptor polypeptide encoding portion. The encoded opiorph receptor polypeptide(s) may be expressed by using any suitable vectors and host cells as explained herein or otherwise known to those skilled in the art.

Vectors will often include one or more replication systems for cloning or expression, one or more markers for selection in the host such as, for example, antibiotic resistance, and one or more expression cassettes. The inserted coding sequences may be synthesized, isolated from natural sources, prepared as hybrids, or the like. Ligation of the coding sequences to the transcriptional regulatory sequences may be achieved by methods known to those skilled in the art. Suitable host cells may be transformed/transfected/ infected by any suitable method including electroporation, $CaCl_2$ mediated DNA uptake, fungal infection, microinjection, microprojectile, or the like.

Suitable vectors for use in practicing the present invention include without limitation YEp352, pcDNAI (InVitrogen), and pRC/CMV (InVitrogen). Suitable host cells include *E. coli,* yeast, COS cells, PC12 cells, CHO cells, GH4Cl cells, and amphibian melanophore cells.

Nucleic acids encoding the opiorph receptor polypeptide (s) may also be introduced into cells by recombination events. For example, such a sequence can be microinjected into a cell, effecting homologous recombination at the site of an endogenous gene encoding the polypeptide, an analog or pseudogene thereof, or a sequence with substantial identity to an opiorph receptor polypeptide-encoding gene. Other recombination-based methods such as non-homologous recombinations, and deletion of endogenous gene by homologous recombination, especially in pluripotent cells, may also be used.

Opiorph Receptor Polypeptides

Opiorph receptor polypeptides OR5 and OR7 are shown in FIG. 2(SEQ ID NO:2). Sequence analysis using Genetics Computer Group software revealed the presence of an open reading frame encoding 367 amino acids, containing seven candidate hydrophobic membrane-spanning domains of 20–24 amino acids that are homologous to those in other, G-protein-linked transmembrane receptors (see FIGS. 3 (SEQ ID NO:2),(SEQ ID NO:3), (SEQ ID NO:4), (SEQ ID NO:5), and (SEQ ID NO:6) and 4). Additionally, the sequence contains four consensus sequences for asparagine-linked glycosylation, as well as serine and threonine residues that are contained in possible intracellular domains and are present within local sequence contexts favorable for phosphorylation by protein kinases A and C. The smaller polypeptide encoded by the splice variant lacks 28 amino acids, (SEQ ID NO:6) including a glycosylation consensus sequence, but is otherwise identical to the larger polypeptide.

Several features of the OR7 structure are consistent with specific functional implications. The size of the third putative intracellular loop predicted by the cDNA is modest, consistent with sizes of the homologous segments in the seven transmembrane domain receptors that do not couple to adenylate cyclase stimulating G proteins. Although many residues lying in transmembrane regions are conserved, the OR7 sequence (SEQ ID NO:2) contain a glutamine at position 305 instead of the histidine that lies in comparable positions in the mu, kappa, and delta opiate receptor sequences. The 28 additional amino acids (SEQ ID NO:6) encoded by the longer splice variant separate a number of negatively charged residues in the putative third extracellular segment from each other.

The present invention also encompasses function-conservative variants as explained above of the amino acid sequences in FIG. 2 (SEQ ID NO:2). Furthermore, fragments of the polypeptide greater than 20 amino acids in length may also exhibit functional properties characteristic of the intact native molecule, for example, the capacity to bind particular ligands.

Opiorph receptor polypeptides may be isolated from any source, such as, for example, native sources in rat tissues or heterologous cells programmed to produce the polypeptide by recombinant DNA methods. Alternately, the polypeptide (s) or peptide fragments thereof can be synthesized in a cell-free context. Peptides of up to 50 amino acids can be chemically synthesized, and larger polypeptides can be synthesized using cell-free translation systems.

Opiorph receptor polypeptides may be modified by methods known in the art. For example, the polypeptides may be phosphorylated or dephosphorylated, glycosylated or deglycosylated, acylated or deacylated, and the like.

In addition, opiorph receptor polypeptides may be expressed as fusion proteins incorporating heterologous sequences. Appropriate fusion partners include sequences useful for immobilization and purification. For example, sequences derived from glutathione-S-transferase (GST) provide a binding site for immobilized glutathione, and sequences that form an epitope recognized by an available monoclonal antibody (e.g. 12CA5 monoclonal antibody) provide a binding site for the immobilized antibody.

Opiorph Receptor Antibodies

Antibodies that are specific for the opiorph receptor polypeptide(s) are provided. These antibodies may be polyclonal or monclonal, and may distinguish the opiorph receptor polypeptide(s) from other opioid receptors or other transmembrane proteins, discriminate opiorph receptor polypeptide (s) from different species, identify associational or other functional domains, and the like.

Such antibodies are conveniently made using the methods and compositions disclosed in Harlow and Lane, *Antibodies, A Laboratory Manual,* Cold Spring Harbor Laboratory, 1988, as well as immunological and hybridoma technologies known to those in the art.

Where natural or synthetic opiorph receptor-derived peptides are used to induce a specific immune response, the peptides may be conveniently coupled to an suitable carrier such as KLH and may be administered in a suitable adjuvant such as Freunds. Preferably, selected peptides are coupled to a lysine core carrier substantially according to the methods of Tam (1988) *Proc Natl Acad Sci USA* 85, 5409–5413. The resulting antibodies may be modified to a monovalent form, such as, for example, Fab, FAB', or FV. Anti-idiotypic antibodies, especially internal imaging anti-idiotypic antibodies, may also be prepared using known methods.

For example, purified opiorph receptor polypeptide(s) can be used to immunize mice. Subsequently; the mice spleens are removed. Splenocytes are used to form cell hybrids with myeloma cells and to obtain clones of antibody-secreted cells according to techniques that are known in the art. The resulting monoclonal antibodies are screened for their ability to bind immobilized opiorph receptor(s) or peptide fragments thereof.

In another example, peptides corresponding to different extracellular domains of the opiorph receptor polypeptide(s) are used as immunogens, and the resulting monoclonal antibodies are screened for their activity in inhibiting the binding of ligands to cells expressing the opiorph receptor polypeptide(s).

Anti-opiorph receptor polypeptide antibodies can be used to identify, isolate, and purify opiorph receptor polypeptide (s) from different sources and to perform subcellular and histochemical localization studies.

Applications

The polypeptides and nucleic acids sequences above can be used in the discovery, design, and development of pharmacologically useful opioid or opioid-like agonists and antagonists or unrelated non-opioid ligands. They can also be used in the design of diagnostic tests for pathological conditions influenced by the presence or absence of opioiph receptor polypeptide function.

For example, the cloned receptor polypeptide(s), or fragments thereof, can be expressed in a heterologous cell in which it can achieve a proper transmembrane orientation and an appropriate localization in the plasma membrane. Examples of suitable cells include COS cells, PC12 cells, CHO cells, Xenopus oocytes, and amphibian melanophore cells. The ability of the expressed polypeptide(s) to bind different ligands can be assessed either by measurement of binding of radiolabelled ligand directly using methods that are standard in the art followed by analysis by, for example, Scatchard analysis or by measurement of the ability of a ligand to alter forskolin-stimulated adenylate cyclase activity. For example, morphine (an exemplary opioid) inhibits the forskolin-stimulated adenylate cyclase activity of the rat or human mu-OR1 opioid receptor and also inhibits $IP_3$ production. Alternatively, in amphibian melanophore cells, a number of G-protein-regulated activities can be easily assessed by visually monitoring the effect of ligands on melanophore distribution within the cells (Jayawickreme, C. K. et al., (1994), *Proc. Natl.Acad. Sci. USA* 91:1614–1618).

In another embodiment, nucleic acid probes are prepared that are specific for the opiorph receptor polypeptide(s) and are used to measure the level of expression of opiorph receptor polypeptide mRNA in different tissues and under different physiological and/or pathological situations. The probes are labelled using a radioactive, fluorescent, or enzymatic label, and are used as direct hybridization probes in a Northern blot. Alternately,. the probes can serve as primers for coupled reverse transcription-polymerase chain reaction, using RNA from the tissue as a template. This results in selective amplification of opiorph receptor related polynucleotide sequences only in tissues in which they are expressed.

Additionally, mutations can be introduced into the sequence of the opiorph receptor polypeptide(s). The mutated sequences are then expressed in a heterologous cell and the structure and function of the variants can be tested. Mutations in the predicted extracellular domains of the polypeptide should alter the opiorph receptor polypeptide(s) ability to bind ligands, while mutations in the predicted intracellular domains, including particular serine and threonine residues, will alter its ability to respond to ligand binding by initiating a biochemical signalling cascade within the cell.

DESCRIPTION OF THE PREFERRED EMBODIMENTS

The following examples illustrate the invention without limitation.

Example 1
Cloning and Sequencing of Opiorph Receptor cDNA

A. Polymerase Chain Reaction

Two degenerate oligonucleotide primers were prepared using an automated oligonucleotide synthesizer. The first, 5'-ACGATGAA(GC)AC(TGA)GCCACCACCA-3'(SEQ ID NO:7), was derived from the unique amino acid sequence VLVVVAVFIV (SEQ ID NO:8) corresponding to amino acids 325–334 of the rat brain mu opioid receptor. The second primer, 5'-CTTCAA(TC)CTGGC(TC)TTGCCTGAT-3'(SEQ ID NO:9), corresponds to amino acids 89–95 derived from the predicted second transmembrane domain, of the murine delta opioid receptor.

PCR reactions were carried out using rat genomic DNA as a template and the Taq polymerase PCR kit (Perkin-Elmer/Cetus, Inc.). The reactions included 20 ng of genomic DNA and 1 µg of each primer. The thermal cycling protocol was as follows: 94° C., 1 minute, followed by 35 cycles of 94.5° C., 20 seconds; 49° C., 45 seconds; 72° C., 45 seconds. This was followed by incubation at 72° C. for 10 minutes, after which the samples were placed on ice.

Resolution of the PCR products on a 1 % agarose gel revealed the presence of products in the range of 500–600 bp in length.

The PCR products from the first reaction were then re-amplified, using identical primers and conditions as above. The products of the second PCR reaction were separated by electrophoresis in a 1% agarose gel, and discrete products were excised and purified on glass beads using the Gene-Clean kit (Bio-101). The purified fragments were then subcloned into the pCR-II vector (InVitrogen) and amplified in *E. coli*.

Bacterial colonies transformed with the pCR-II vector were subjected to alkine lysis to isolate plasmid DNA. The DNAs were then sequenced using the dye primer automated sequencing system (Applied Biosystems, Model 373A). Sequence analyses and alignments were performed using the MacVector software package (I.B.I.).

This approach identified an unspliced opiorph receptor-encoding sequence corresponding to OR5 (see FIG. 1)(SEQ ID NO:1). This sequence contains the 84 nucleotides that are absent from the smaller splice variant.

B. Library screening pPCR4A is a 700 base pair (bp) pPCRII (InVitrogen) subclone of a partial mu opiate receptor cDNA amplified from single stranded rat brain CDNA. The 700 bp pPCR4A insert. was excised with EcoRI, radiolabelled by random priming, and used to isolate cDNAs from a size-selected rate cerebral cortex lambda ZAP CDNA library. Sequence analyses of the inserts from autoexcised plasmids revealed apparent partial sequences with substantial homology to other cloned opiate receptors, including a 2.8 kb cDNA, from which a 5' 500 bp fragment was isolated using HindIII. This fragment was radiolabeled by random priming and was used to isolate other more 5' cDNAs including a 3 kb cDNA. Inserts from the two clones were cut and ligated to form a fused clone encoding the smaller, splice-variant form of the opiorph receptor (SEQ ID NO:2) i.e. lacking the internal 28 amino acids encoded by the spliced-out oligonucleotide (SEQ ID NO:6)(see FIG. 3).

The present cDNAs add substantially to the diversity of the gene subfamily that contains opiate receptors. The splice variant documented for this receptor represents the first example of differential splicing in this receptor gene subfamily, and suggests an intron-exon border likely to be conserved in several opiate receptor subfamily genes.

Example 2
Tissue Distribution of Opiorph Receptor mRNA

A. Reverse Transcription-Polymerase Chain Reaction

Two oligonucleotide primers were prepared corresponding to nucleotides 51–71 and 546–566 of the sequence of FIG. 1, consisting of 5'-AGGGCACAGACATCCTACTGG-3' (SEQ ID NO:10) and 5'-AGCCTGAAAGC AGACGGACAC-3'(SEQ ID NO:11).

RNA was prepared from rat tissues that were rapidly dissected and frozen at −70° C. and from rat cell lines. The RNAs served as templates for combined reverse-transcriptase-polymerase chain reactions (RT-PCR). The reactions were carried out using an RT-PCR kit (Perkin-Elmer/Cetus) employing rTth bifunctional polymerase. Synthesis of single-stranded cDNA was performed using 100–200 ng of RNA and 2 µg of the 3' primer. After incubation at 65° C. for 10 minutes, chelating buffers, MgCl$_2$, and 0.75 μg of the 5' primer were added. The thermal cycling sequence Was as follows: 94° C., 1 minute, followed by 35 cycles of 94.5° C., 20 seconds; 60° C., 20 seconds; and 72° C., 60 seconds. The reaction mixtures were then chilled, and the products were analyzed on a 1% agarose gel in tris-borate-EDTA buffer.

Figure 5:
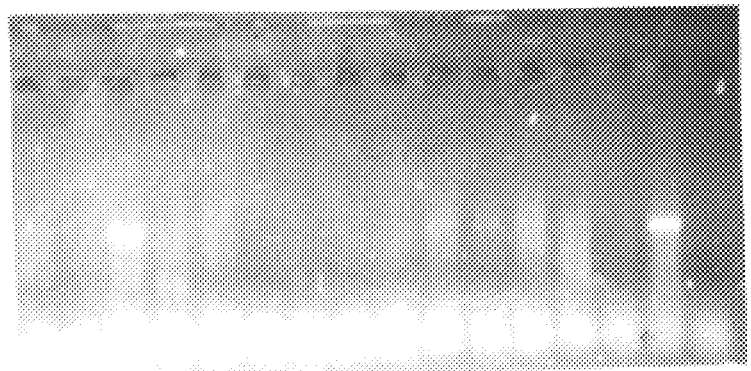
FIG. 5 is an illustration of an autoradiogram showing the tissue distribution of mRNA encoding an opiorph receptor polypeptide, as determined by reverse transcription-polymerase chain reaction (RT-PCR) using, as a template, RNA derived from different rat tissues and cell lines. The RT-PCR products were resolved in an agarose gel. The left lane contains molecular mass markers, after which the lanes are numbered sequentially 1–16 from left to right.

Results are shown in FIG. 5 and indicate that opiorph receptor is expressed in brain, pituitary, thymus, stomach, muscle, and fat tissues.

In another experiment, reverse transcription-PCR was performed using as template 5 μg of total RNA extracted from different tissues and oligonucleotide primers 5'-ACCCTGGTCTTGCTAACA-3' (SEQ ID NO:12) and 5'-CAGCACCAGTCGAGTGAT-3' (SEQ ID NO:13). Single-stranded cDNA was amplified by 35 cycles of 94° C. for 1 minute, 55° C. for 1 minute, and 92° C. for 1 minute), with separation of PCR products by 2% agarose gel electrophoresis, transfer to nylon membranes, hybridization overnight with a $^{32}$P-labeled opiorph cDNA probe at 42° C., followed by phosphorimaging.

Figure 6A:
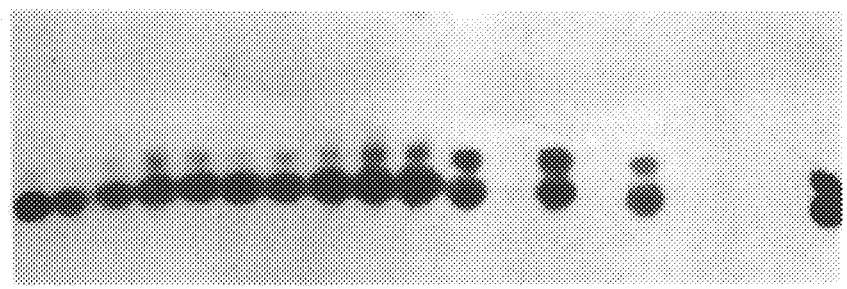
FIG. 6A is an illustration of an autoradiogram showing the tissue distribution of mRNA encoding an opiorph receptor polypeptide, as determined by RT-PCR using as a template RNA derived from different rat tissues. The RT-PCR products were resolved in an agarose gel, transferred to nylon membranes, and hybridized with an opiorph receptor polypeptide-specific radiolabelled DNA probe. The tissues used as sources of RNA were as follows: Lane 1, cerebellum; lane 2, cerebral cortex; lane 3, striatum; lane 4, midbrain; lane 5, hippocampus; lane 6, brainstem; lane 7,. olfactory bulb; lane 8, spinal cord; lane 9, thalamus; lane 10, hypothalamus; lane 11, intestine; lane 12, skeletal muscle; lane 13, vas deferens; lane 14, esophagus; lane 15, liver; lane 16, kidney; lane 17, testis; lane 18, adrenal; and lane 19, spleen.
Figure 6B:
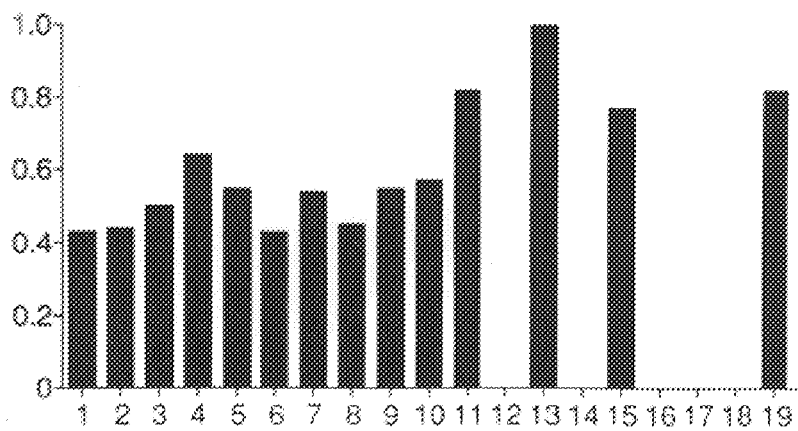
FIG. 6B is an illustration of the ratio between the RT-PCR products derived from the small and large splice variants, respectively. The tissues are as in FIG. 6A. The Y-axis represents the ratio of labelled hybridization probe recognizing the short variant to that recognizing the long variant.

Results are shown in FIGS. 6A and 6B. FIG. 6A indicates that two splice variant products were detected in various brain regions, as well as in several peripheral tissues such as intestine, skeletal muscle, vas deferens and spleen. FIG. 6B indicates that the ratio between the two splice variants also varies among the brain regions and peripheral tissues examined.

B. Northern Analysis

Total RNA was prepared from rat tissues that were rapidly dissected and frozen at −70° C. 20 μg of each RNA were resolved in agarose-formamide gels. The separated RNA species were then transferred to nylon membranes. Blots were hybridized with opiorph receptor cDNA radiolabelled with $^{32}$P by random priming. Hybridizations were carried out in 50% formamide, 5×SSC, 50 mM NaPO$_4$, 1% SDS, 2.5×Denhardt's solution, and 200 μg/ml salmon sperm DNA at 42° C. overnight. The filters were then washed twice in 0.1×SSC/0.1% SDS for 30 minutes at 65° C. Radioactive patterns were identified using a phosphorimaging device (Molecular Dynamics) following overnight exposures.

Figure 7:
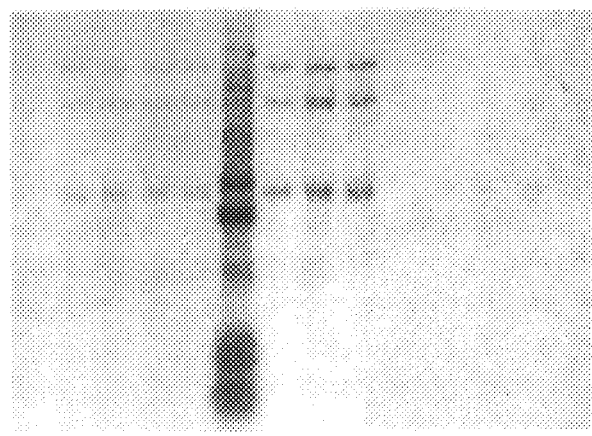
FIG. 7 is an illustration of a Northern blot of RNA derived from rat thalamus (TH, lanes 11–4), hypothalamus (HV, lanes 5–8), and striatum (ST, lanes 9–12) hybridized to a radiolabelled opiorph receptor polypeptide DNA probe.

Results are illustrated in FIG. 7. This analysis revealed that the highest levels of opiorph receptor expression are in the hypothalamus. At least three hybridizing mRNA species are observed in this brain region and in brainstem, midbrain, cerebral cortex, thalamus and hippocampus, but not in striatum or cerebellum.

Conceivably, two of these three mRNAs could represent products of different genes closely related to OR7 in sequence. Alternately, mRNA splicing and/or polyadenylation site usage events in the gene's untranslated regions could yield the significant differences in transcript molecular mass noted in Northern analyses.

Example 3

Heterologous Expression of Opiorph Receptor in COS cells

COS cells were transfected by electroporation with 20 4g/10$^7$ cells of opiorph cDNA which had been cloned into the pcDNAI vector (InVitrogen). Transfected cells were plated in Dulbecco's modified minimal essential medium (GIBCO, Grand Island, N.Y.) containing 10% fetal bovine serum and maintained at 37° C. in a humidified atmosphere containing 5 % CO$_2$.

Expression of opiorph receptor polypeptide(s) was assessed by measurement of specific ligand binding. Alternatively, expression of opiorph receptor polypeptide(s) may be assessed by RNA extraction and RT-PCR according to the procedure of Example 2 above or immuno assay with antibodies specific to the opiorph receptor(s).

Example 4

Analysis of Ligand Binding Characteristics of Opiorph Receptors

COS cells transfected with opiorph receptor cDNA or, as a control, rat or human mu opiate receptor cDNA were harvested. Membranes were prepared by homogenization at 4° C. in 50 mM Tris buffer and centrifugation at 1000×g for 10 minutes. The supernatant was then recovered and subjected to centrifugation at 46,000×g for 30 minutes. The membrane-containing pellet was recovered, and fractions corresponding to 50 μg of protein were resuspended in 0.5 ml of Tris buffer and incubated with different radiolabelled ligands.

The ligands were: [$^3$H]bremazocine (29.2 Ci/mmol, NEN), [$^3$H]naloxone (47.2 Ci/mmol, NEN), [$^3$]diprenorphine (29 Ci/mmol, NEN), [$^3$H]DAMGO ([D-Ala2,N-Methyl-Phe4,Glyol[5]enkephalin; 60 Ci/mmol, Amersham), [$^3$H]DPDPEpCl ([D-Pen2,4'-Cl-Phe4,D-Pea5] enkephalin; 51 Ci/mmol, NEN), [$^3$H]DADLE (D-Ala2,D-LeU5 enkephalin; 37 Ci/mmol, NEN), [$^3$H] ethylketocyclazocine (28.5 Ci/mmol, NEN), [$^3$H]etorphine (38.7 Ci/mmol, NEN), [$^3$]buprenorphine (13.4 Ci/mmol, RBI). [$^{125}$I]β-endorphin (2,000 Ci/mmol, Amersham) and [$^3$]U-69,593 (57 Ci/mmol, Amersham).

Incubations were for 150 minutes at 22° C., after which the reactions were filtered through GFB filters (Whatman). The filters were washed three times with Tris buffer at 4° C. Radioactivity associated with the filters was determined by liquid scintillation counting, and data were analyzed using EBDA and LIGAND (Munson et al., *Anal. Biochem.* 107:220, 1980).

Under conditions in which robust binding to rat or human μOR1 polypeptides was observed, no definitive binding of the above ligands to opiorph receptor polypeptide(s) was observed. No specific radioligand binding above background levels was observed in eight of ten experiments using cells expressing the smaller splice variant of the opiorph receptor or in four of four experiments using cells expressing the larger splice variant. In two experiments, modest naloxone-displacable diprenorphine, bremazocine, and β-endorphin binding above background values was noted in cells expressing the smaller splice variant. However, intermittent naloxone-displacable binding of naloxone and β-endorphin was also observed in mock-transfected COS cells in several negative control experiments. Neither radiolabeled diprenorphine, bremazocine, not β-endorphin displayed specific binding in eight additional experiments. Neither ethylketocyclazocine, naloxone, DAMGO, DPDPE, U,69,693, ctorphine, buprenorphine, not DADLE resulted in specific binding in any experiment.

COS cells transfected with either the large or small splice variant of OR7 failed to display consistent opiate-induced alteration in forskolin-stimulated adenylate cyclase activity. In 14 experiments in which morphine-inhibited adenylate cyclase activity in COS cells expressing rat or human mu opiate receptor cDNAs served as positive controls, eight of 10 experiments revealed no opiate-mediated inhibition of forskolin-stimulated cyclase activity in cells expressing the smaller splice variant of OR7, and four of four experiments revealed no opiate-mediated inhibition of forskolin-stimulated cyclase activity in cells expressing the larger splice variant of OR7. In two experiments, bremazocine, buprenorphine, etorphine and β-endorphin did elicit modest naloxone-reversible inhibition of forskolin-stimulated cyclase activity in cells expressing the smaller splice variant. However, intermittent naloxone-reversible β-endorphin effects were also noted in some experiments in mockfransfected cells. Neither bremazocine, buprenoiphine, etorphine nor endorphin altered forskolin-stimulated cAMP levels in eight additional experiments; neither DADLE, Dynorphin A, morphine, nor U50,488 altered cAMP levels in any experiment.

Deposit of Biological Materials

The following biological materials were deposited with the American type Culture Collection, 12301 Park Lain Drive, Rockville, Md. 20857 as follows:

Strain OZ86 deposited Dec. 23, 1993,
Accession Number ATCC 69525.

All patents, applications, articles, publications, and test methods mentioned above are hereby incorporated by reference.

Many variations of the present invention will suggest themselves to those skilled in the art in light of the above detailed description. Such obvious variations are within the full intended scope of the appended claims.

---

We claim:

1. A method for detecting the expression, in a tissue, of mRNA encoding a polypeptide having an amino acid sequence comprising amino acid residues 88–269 of the amino acid sequence of SEQ ID NO:2, said method comprising:

(a) selecting at least one oligonucleotide sequence unique to said polypeptide, wherein said sequence comprises from about 15 to about 30 nucleotides;

(b) synthesizing said oligonucleotides;

(c) hybridizing said oligonucleotide to total mRNA isolated from said tissue under stringent conditions; and (d) detecting said hybridization.

2. A method as defined in claim 1, wherein said detecting step comprises polymerase chain reaction.

* * * * *